United States Patent
Tovey et al.

(10) Patent No.: US 6,827,712 B2
(45) Date of Patent: Dec. 7, 2004

(54) ROBOTIC ARM DLUS FOR PERFORMING SURGICAL TASKS

(75) Inventors: H. Jonathan Tovey, Monore, CT (US); Keith Ratcliff, Newtown, CT (US); Kenneth E. Toso, Wilton, CT (US); Peter W. J. Hinchliffe, New Haven, CT (US)

(73) Assignee: United States Surgical Corporation, Norwalk, CT (US)

( * ) Notice: Subject to any disclaimer, the term of this patent is extended or adjusted under 35 U.S.C. 154(b) by 64 days.

(21) Appl. No.: 09/804,531

(22) Filed: Mar. 12, 2001

(65) Prior Publication Data

US 2001/0014801 A1 Aug. 16, 2001

Related U.S. Application Data

(62) Division of application No. 09/099,740, filed on Jun. 18, 1998, now Pat. No. 6,231,565.
(60) Provisional application No. 60/049,923, filed on Jun. 18, 1997.

(51) Int. Cl.[7] .............................................. A61B 17/00
(52) U.S. Cl. ......................................... 606/1; 600/102
(58) Field of Search ..................... 606/1, 130; 600/102

(56) References Cited

U.S. PATENT DOCUMENTS

| | | |
|---|---|---|
| 4,411,266 A | 10/1983 | Cosman |
| 4,508,253 A | 4/1985 | Green |
| 4,565,200 A | 1/1986 | Cosman |
| 4,907,589 A | 3/1990 | Cosman |
| 4,955,862 A | 9/1990 | Sepetka |
| 4,966,597 A | 10/1990 | Cosman |
| 4,979,949 A | 12/1990 | Matsen, III et al. |
| 5,040,715 A | 8/1991 | Green et al. |
| 5,084,057 A | 1/1992 | Green et al. |
| 5,095,915 A | 3/1992 | Engelson |
| 5,122,137 A | 6/1992 | Lennox |
| 5,154,717 A | 10/1992 | Matsen, III et al. |
| 5,187,796 A | 2/1993 | Wang et al. |
| 5,236,432 A | 8/1993 | Matsen, III et al. |
| 5,289,963 A | 3/1994 | McGarry et al. |
| 5,300,081 A | 4/1994 | Young et al. |
| 5,304,131 A | 4/1994 | Paskar |
| 5,315,996 A | 5/1994 | Lundquist |
| 5,329,923 A | 7/1994 | Lundquist |
| 5,334,145 A | 8/1994 | Lundquist et al. |
| 5,397,323 A | 3/1995 | Taylor et al. |
| 5,403,311 A | 4/1995 | Abele et al. |
| 5,403,328 A | 4/1995 | Shallman |
| 5,433,739 A | 7/1995 | Sluijter et al. |
| 5,437,288 A | 8/1995 | Schwartz et al. |
| 5,441,483 A | 8/1995 | Avitall |
| 5,470,006 A | 11/1995 | Rodak |
| 5,477,856 A | 12/1995 | Lundquist |

(List continued on next page.)

FOREIGN PATENT DOCUMENTS

| | | |
|---|---|---|
| EP | 0 521 595 B1 | 2/1992 |
| EP | 064731 A2 | 4/1995 |
| WO | WO 93/04722 | 3/1993 |
| WO | WO 00/71043 A1 | 11/2000 |
| WO | WO 01/26570 A1 | 4/2001 |

Primary Examiner—Beverly M. Flanagan

(57) ABSTRACT

Disposable loading units (DLUs) configured for mounting to a robotic arm for performing at least one surgical task are presented. Each DLU includes an attachment platform having at least one connector for engaging at least one connector on a distal end of the robotic arm for connecting the DLU to the robotic arm, a head portion connected to the attachment platform at one end and configured for housing an electro-mechanical actuation assembly therein, and at least one surgical tool member extending from the head portion and operatively associated with the electro-mechanical actuation assembly for controlling the operation and movement of the at least one surgical tool member. The at least one surgical tool member may include a cutting assembly, an aortic hole punch assembly, a lasing assembly, a coring assembly, or a vascular suturing assembly.

4 Claims, 8 Drawing Sheets

U.S. PATENT DOCUMENTS

| | | | | |
|---|---|---|---|---|
| 5,478,344 A | | 12/1995 | Stone et al. | |
| 5,497,785 A | | 3/1996 | Viera | |
| 5,515,478 A | | 5/1996 | Wang | |
| 5,524,180 A | | 6/1996 | Wang et al. | |
| 5,536,267 A | | 7/1996 | Edwards et al. | |
| 5,545,193 A | | 8/1996 | Fleischman et al. | |
| 5,545,200 A | | 8/1996 | West et al. | |
| 5,553,198 A | | 9/1996 | Wang et al. | |
| 5,571,110 A | | 11/1996 | Matsen, III et al. | |
| 5,571,147 A | | 11/1996 | Sluijter et al. | |
| 5,573,520 A | | 11/1996 | Schwartz et al. | |
| 5,624,398 A | | 4/1997 | Smith et al. | |
| 5,645,520 A | | 7/1997 | Nakamura et al. | |
| 5,657,429 A | | 8/1997 | Wang et al. | |
| 5,728,149 A | | 3/1998 | Laske et al. | |
| 5,746,701 A | | 5/1998 | Noone | |
| 5,748,767 A | | 5/1998 | Raab | |
| 5,754,741 A | | 5/1998 | Wang et al. | |
| 5,762,458 A | * | 6/1998 | Wang et al. | 606/130 |
| 5,785,705 A | | 7/1998 | Baker | |
| 5,792,135 A | | 8/1998 | Madhani et al. | |
| 5,797,900 A | | 8/1998 | Madhani et al. | |
| 5,800,423 A | * | 9/1998 | Jensen | 606/1 |
| 5,807,377 A | | 9/1998 | Madhani et al. | |
| 5,814,038 A | | 9/1998 | Jensen et al. | |
| 5,815,640 A | | 9/1998 | Wang et al. | |
| 5,820,623 A | * | 10/1998 | Ng | 606/1 |
| 5,833,632 A | | 11/1998 | Jacobsen et al. | |
| 5,841,950 A | | 11/1998 | Wang et al. | |
| 5,855,583 A | * | 1/1999 | Wang et al. | 606/130 |
| 5,871,523 A | | 2/1999 | Fleischman et al. | |
| 5,907,664 A | | 5/1999 | Wang et al. | |
| 5,911,036 A | | 6/1999 | Wright et al. | |
| 5,951,546 A | | 9/1999 | Lorentzen | |
| 5,971,976 A | | 10/1999 | Wang et al. | |
| 5,980,504 A | | 11/1999 | Sharkey et al. | |
| 5,983,141 A | | 11/1999 | Sluijter et al. | |
| 6,001,093 A | | 12/1999 | Swanson et al. | |
| 6,004,279 A | | 12/1999 | Crowley et al. | |
| 6,007,550 A | | 12/1999 | Wang et al. | |
| 6,007,570 A | | 12/1999 | Sharkey et al. | |
| 6,024,695 A | | 2/2000 | Taylor et al. | |
| 6,048,339 A | | 4/2000 | Zirps et al. | |
| 6,063,095 A | | 5/2000 | Wang et al. | |
| 6,073,051 A | | 6/2000 | Sharkey et al. | |
| 6,095,149 A | | 8/2000 | Sharkey et al. | |
| 6,099,514 A | | 8/2000 | Sharkey et al. | |
| 6,099,541 A | | 8/2000 | Klopotek | |
| 6,102,850 A | | 8/2000 | Wang et al. | |
| 6,122,549 A | | 9/2000 | Sharkey et al. | |
| 6,126,682 A | | 10/2000 | Sharkey et al. | |
| 6,132,368 A | * | 10/2000 | Cooper | 600/102 |
| 6,132,441 A | | 10/2000 | Grace | |
| 6,146,380 A | | 11/2000 | Racz et al. | |
| 6,161,048 A | | 12/2000 | Sluijter et al. | |
| 6,231,565 B1 | * | 5/2001 | Tovey et al. | 606/1 |
| 6,264,650 B1 | | 7/2001 | Hovda et al. | |
| 6,346,072 B1 | * | 2/2002 | Cooper | 606/1 |
| 6,364,888 B1 | | 4/2002 | Niemeyer et al. | |
| 6,436,107 B1 | | 8/2002 | Wang et al. | |
| 6,463,361 B1 | | 10/2002 | Wang et al. | |
| 6,496,099 B2 | | 12/2002 | Wang et al. | |

* cited by examiner

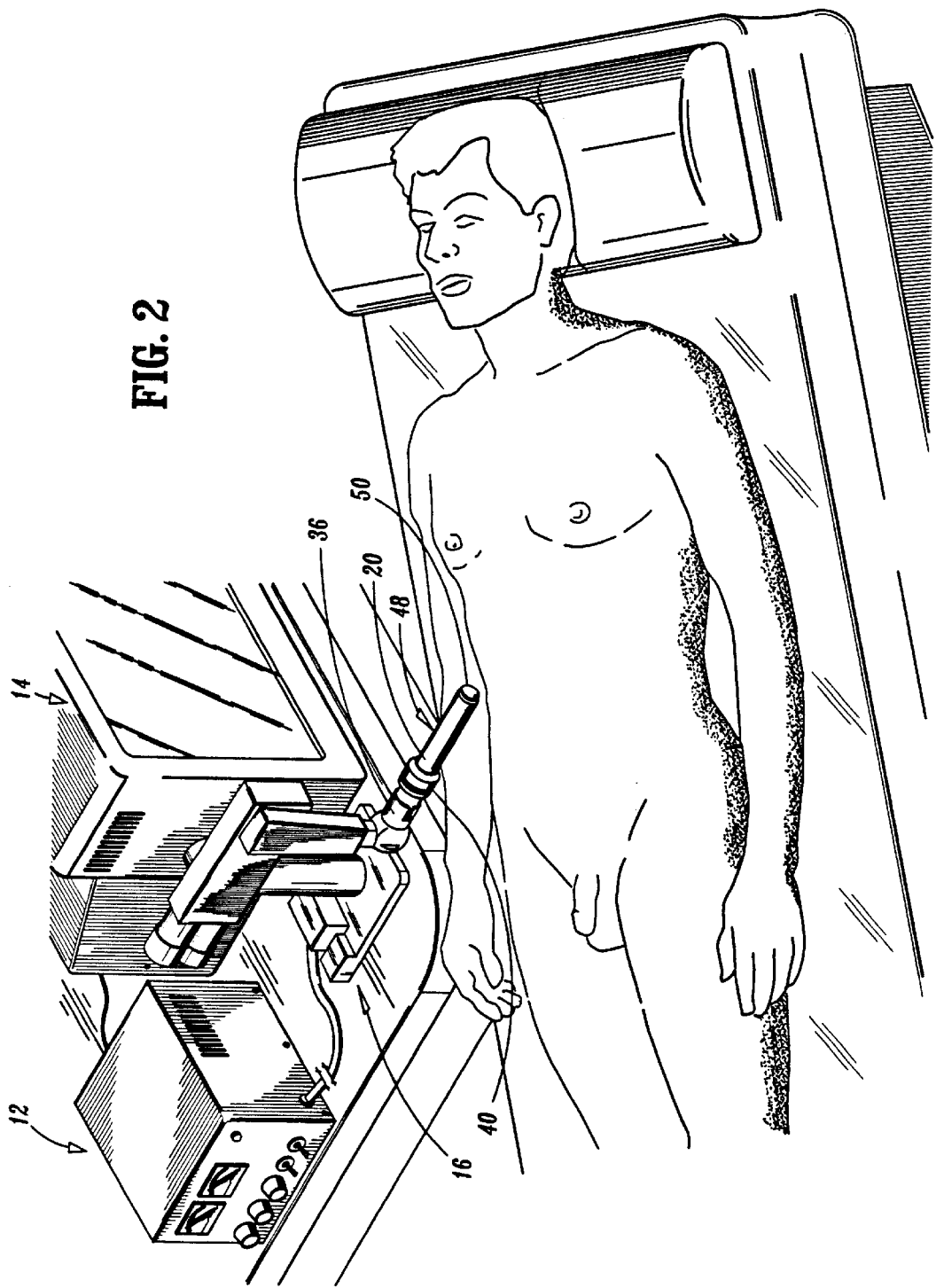

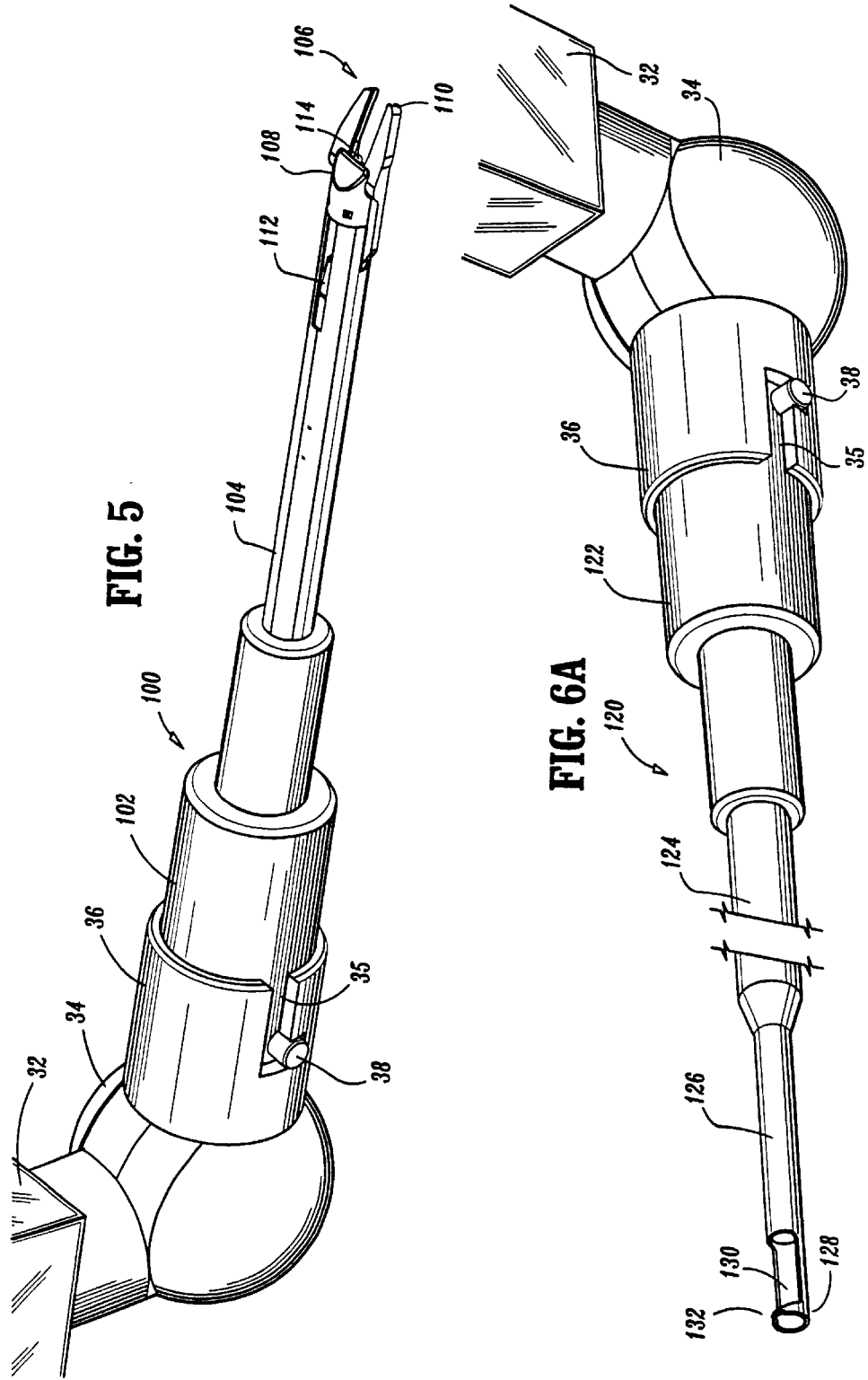

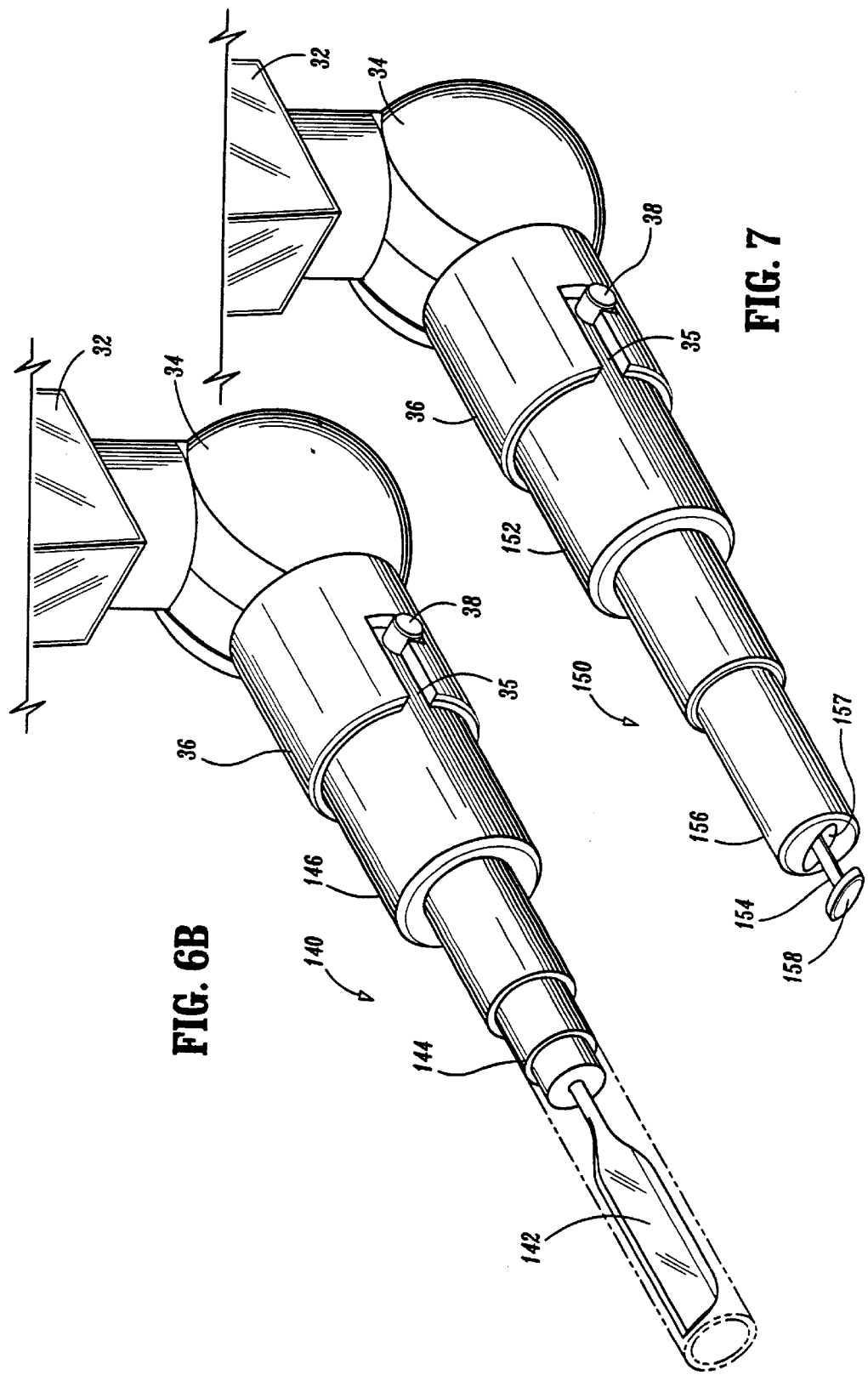

ROBOTIC ARM DLUS FOR PERFORMING SURGICAL TASKS

This application claims priority to a Provisional Application filed on Jun. 18, 1997 having Ser. No. 60/049,923.

BACKGROUND

1. Technical Field

The present disclosure relates to an apparatus and method for performing surgical tasks. In particular, the disclosure relates to disposable loading units (DLUs) configured for mounting to a robotic arm and having at least one automatically actuated surgical tool for performing a surgical task.

2. Description of Related Art

Accurate and precise manipulation of surgical instruments at or near a surgical site is required during surgical procedures, especially during minimally invasive procedures such as laparoscopic and endoscopic procedures. In laparoscopic and endoscopic surgical procedures, a small incision is made in the patient's body to provide access for a tube or cannula device. Once extended into the patient's body, the cannula allows insertion of various surgical instruments for acting on organs, blood vessels, ducts, or body tissue far removed from the incision site. Such instruments may include apparatus for applying surgical clips as disclosed in U.S. Pat. No. 5,084,057; apparatus for applying surgical staples as disclosed in U.S. Pat. Nos. 5,040,715 and 5,289,963; and apparatus for suturing body tissue as disclosed in U.S. Pat. No. 5,403,328.

In minimally invasive procedures, the ability to perform surgical tasks is complicated due to limited maneuverability and reduced visibility. Therefore, a need exists for an apparatus and a procedure that enables the remote actuation of surgical instruments during minimally invasive procedures in a consistent, easy and rapid manner.

In non-laparoscopic and non-endoscopic procedures, accurate and precise manipulation and operation of surgical instruments is also required. For example, in a transmyocardial vascularization (TMR) procedure, wherein holes are formed in the heart wall to provide alternative blood flow channels for ischemic heart tissue, careful advancement and control of a lasing or coring device is necessary to form holes in the ischemic areas of the heart tissue.

In other cardiovascular procedures such as laser angioplasty wherein an optical fiber is inserted and advanced into a patient's vasculature to apply laser energy to obstructions and/or restrictions typically caused by plaque build-up, precise manipulation and operation is also required. Both continuous wave and pulsed high energy lasers have been used to provide the vaporizing laser energy. Insuring the plaque is actually ablated and not just pushed aside is important to prevent or delay restenosis.

The advent of computer imaging systems have enabled surgeons to precisely position and map the direction of travel of a surgical instrument prior to the utilization of the instrument in the operation. For example, an imaging system can locate the exact location of a lesion within a patient and allocate X, Y and Z coordinates to that lesion in space. A coring device can then be manually advanced to that location to slice the distal flat end face of the core so that a complete specimen can be removed for biopsy.

Robotic systems have also been developed to aid a surgeon in precisely mounting and positioning surgical instruments to perform a surgical task. For example, U.S. Pat. No. 5,571,110 to Matsen, III et al. discloses an orthopedic saw guide for confining the blade of a surgical saw to movement in a single plane while allowing translational and rotational movement of the blade within the plane to facilitate the performance of a surgical bone alteration task. The saw guide is positioned relative to a patient's bone by a robot-aided system.

However, known robotic systems, such as the saw guide disclosed in the Matsen et al. '110 patent, are typically limited to specific surgical tasks and are not adaptive for performing a wide variety of surgical tasks. Therefore, there is a need for a robotic system for aiding a surgeon to perform a wide variety of surgical tasks.

Another disadvantage of known robotic systems having surgical application is that the surgeon is required to manually control the position and operation of the surgical instrument. For example, systems have been developed wherein the surgeon is fitted with a mechanism which translates the surgeon's movements into mechanical movements whereby servo motors are actuated to manipulate the surgical instrument. For example, U.S. Pat. No. 5,624,398 to Smith et al. discloses a robotic system having a pair of articulate robotic arms responsive to the surgeon's movements during the surgery. However, any error in the surgeon's movements results in undesired manipulation of the robotic arms. Therefore, a fully automatic robotic system for aiding a surgeon to perform a wide variety of surgical tasks would be advantageous.

Another disadvantage with known robotic systems is their inability to remotely operate a conventional surgical tool, such as an apparatus for applying surgical staples or an apparatus for suturing body tissue which is mounted to the robotic arm.

Therefore, it would be advantageous to provide disposable loading units (DLUs) configured for mounting to a robotic arm of a robotic system and having at least one surgical tool extending from one end for performing a surgical task. The DLU would be actuated by an actuation assembly operatively associated with the robotic arm for controlling the operation and movement of the DLU. The DLU would include an electro-mechanical assembly operatively associated with the actuation assembly for controlling the operation and movement of the surgical tool.

SUMMARY

The subject disclosure is directed to disposable loading units configured for mounting to a robotic arm and having at least one automatically actuated surgical tool for performing a surgical task. The robotic arm acts on the DLUs with the dexterity and mobility of a surgeon's hand and can be programmed via an actuation assembly to actuate the surgical tool to perform the surgical task. Actuation commands are transmitted by electrical signals via cables from the actuation assembly to an electro-mechanical assembly within the DLUs. The electro-mechanical assembly within each DLU is configured to move and operate the surgical tool for performing the surgical task. For example, the electro-mechanical assembly may include servo motors for advancing, rotating and retracting a coring member of a coring DLU device; for harmonically oscillating a scalpel of a cutting DLU device; or for pivotally moving a suturing needle positioned on an axis of a longitudinal casing of a suturing DLU device.

One DLU presented and configured for mounting to the robotic arm is a coring DLU device for minimally invasive surgery, such as removing a specimen for biopsy. Still another DLU presented is a lasing DLU device for performing surgical procedures entailing the use of laser energy, such as TMR and angioplasty. Additional DLUs presented include a surgical fastener applying DLU device, a vessel clip applying DLU device, a cutting DLU device, a hole punching DLU device, and a vascular suturing DLU device.

BRIEF DESCRIPTION OF THE DRAWINGS

Various robotic arm DLUs for performing surgical tasks will be described hereinbelow with reference to the drawings wherein:

FIG. 2 illustrates a surgeon utilizing the apparatus of FIG. 1 in the performance of a surgical procedure;

FIG. 5 is a perspective view of a vessel clip applying DLU device;

FIG. 6A is a perspective view of a first embodiment of a cutting DLU device;

FIG. 6B is a perspective view of a second embodiment of a cutting DLU device;

FIG. 7 is a perspective view of a hole-punching DLU device; and

DETAILED DESCRIPTION OF THE PREFERRED EMBODIMENTS

The robotic arm disposable loading units (DLUs) and accompanying robotic system of the present disclosure shall be discussed in terms of performing a variety of surgical tasks, which include but not limited to endoscopic, arthroscopic and/or laparoscopic procedures. The present disclosure introduces and discusses several DLUs, which include a coring DLU, two cutting DLUs, an aortic hole-punching DLU, a lasing DLU, a fastener applying DLU, and a vascular suturing DLU. However, the present disclosure should not be construed to limit the present application to only these DLUs.

Figure 1:
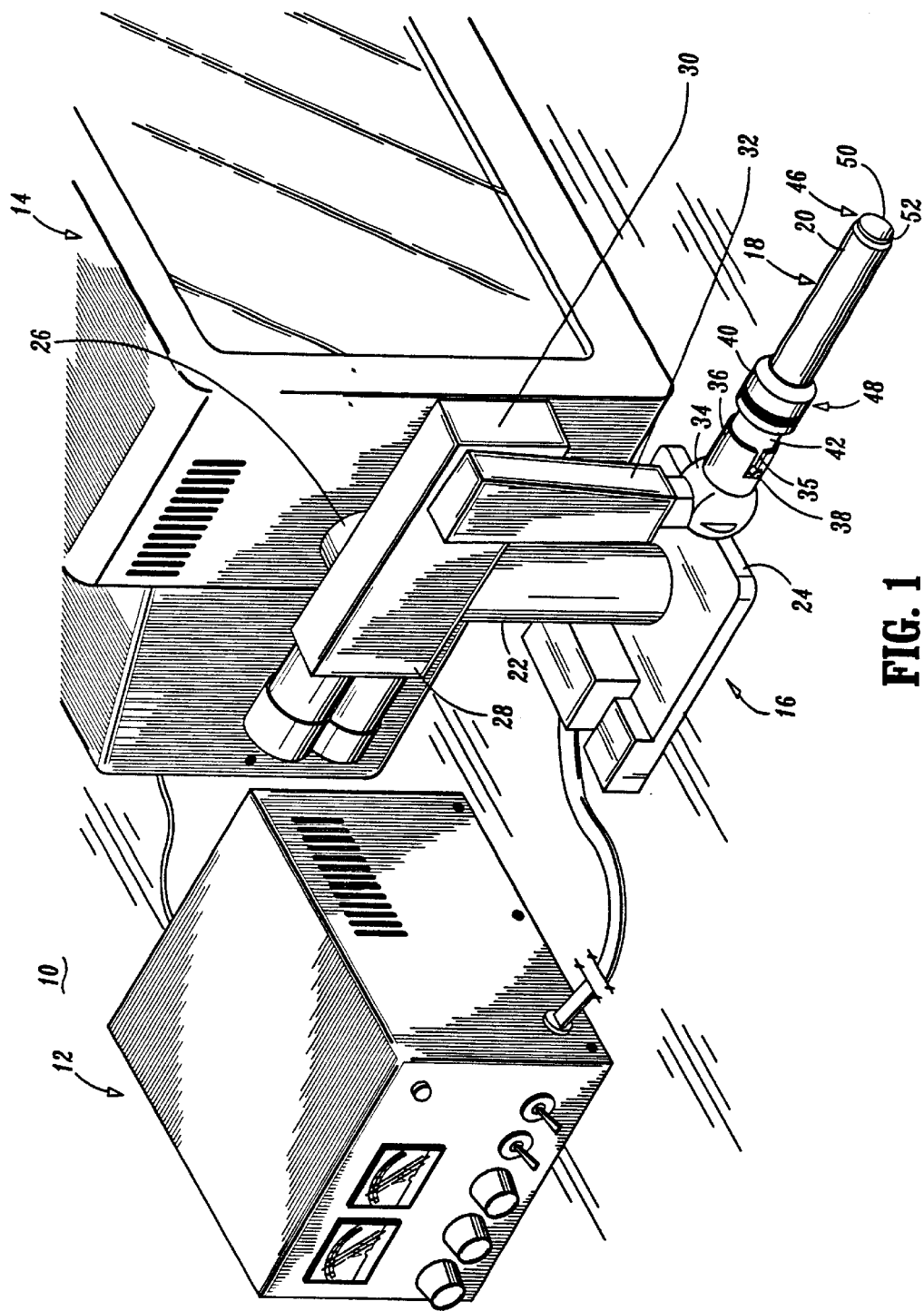
FIG. 1 is a perspective view of a robotic system constructed in accordance with the present disclosure and illustrating a coring DLU device.

Referring now to the drawings wherein like reference numerals indicate similar structural elements, there is illustrated in FIG. 1 a robotic system designated generally by reference numeral 10. Robotic system 10 can be used to performing a wide variety of surgical tasks, such as operate surgical instrumentation within the abdominal cavity of a patient with a fine degree of dexterity and accuracy.

The robotic system 10 includes an actuation assembly 12, a monitor 14, a robot 16, and a DLU 18 releasably attached to the robot 16 and having at least one surgical tool 20 for performing at least one surgical task. The robot 16 includes a trunk 22 extending from a base 24, a shoulder 26 connecting the trunk to an upper arm 28, an elbow 30 connecting the upper arm 28 to a lower arm 32, and a wrist 34 attached to the lower arm 32 from which extends a mounting flange 36. The mounting flange 36 is capable of moving in six degrees of freedom.

Figure 1A:
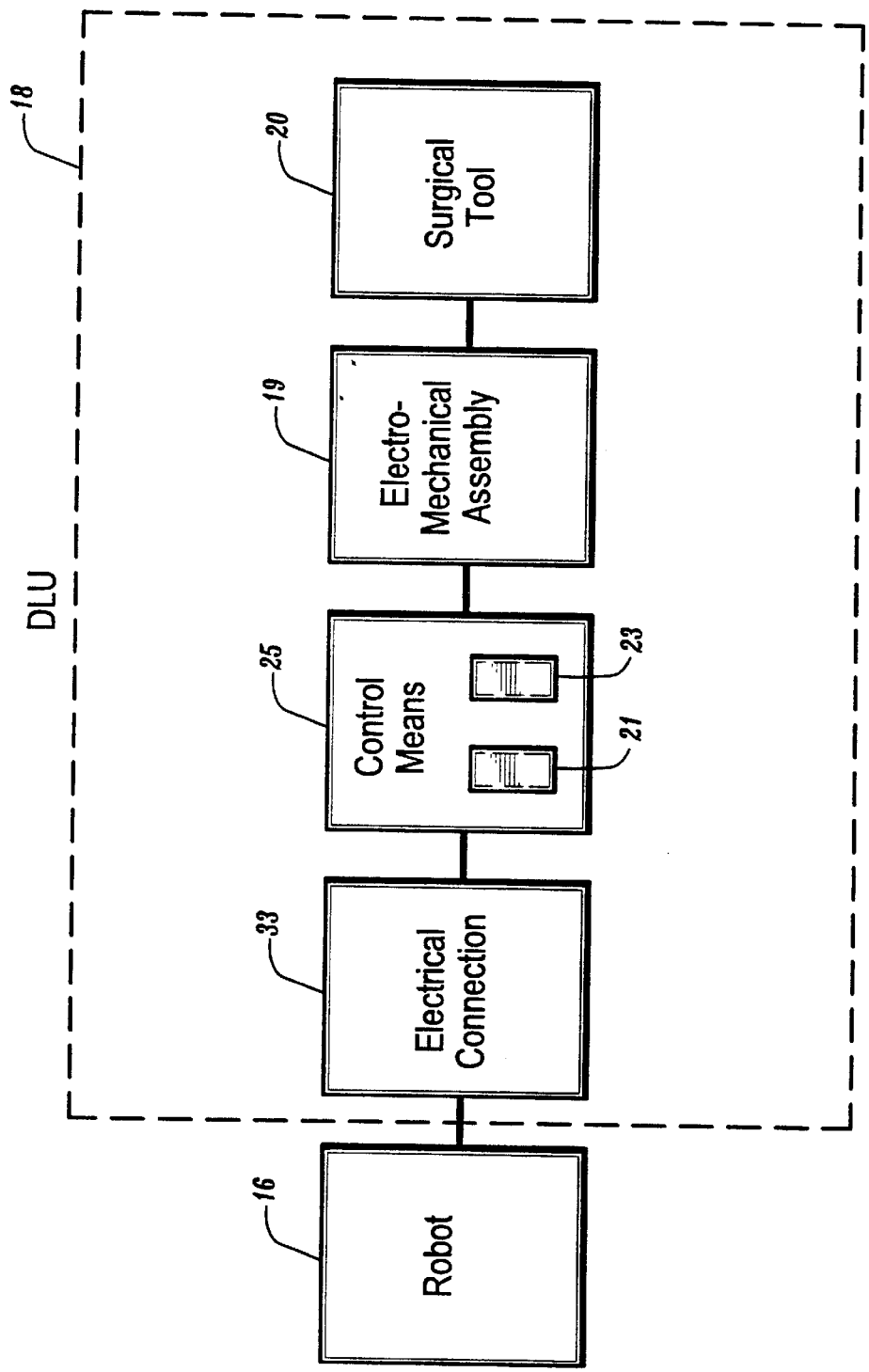
FIG. 1A is a block diagram illustrating the components of a DLU device.

The DLU 18 further includes a head portion 40 for housing an electro-mechanical assembly 19 (FIG. 1A) therein for operating the surgical tool 20 and an attachment platform 42 for releasably attaching the DLU 18 to the robot 16 via the mounting flange 36. The mounting flange 36 includes two slots 35 which matingly engage protrusions 38 of the attachment platform 42 to connect the mounting flange 36 with the DLU 18. Other forms of releasable mechanical attachment of these components are envisioned as well, such as bayonet coupling, tongue and groove arrangements, snap-fit arrangements, interference fit arrangements, and locking screw arrangements. It is also contemplated to provide an electrical connection 33 between the slots 35 and the protrusions 38 for powering the electromechanical assembly 19 as shown by FIG. 1A.

The DLU 18 can be removed from the mounting flange 36 and be replaced with another DLU having a different surgical tool for performing a different surgical procedure. It is also contemplated to design a DLU having several surgical tools capable of performing several surgical procedures where the robot 16 can rotate the mounting flange 36 to select one of the surgical tools of the DLU when required.

In operation, the surgeon controls the actuation assembly 12 to control the movement and operation of the robot 16 and the DLU 18. Depending on the amount of rotation of the knobs 44 on the actuation assembly 12, the actuation assembly 12 transmits electrical signals to the robot 16 to electromechanically operate the moveable parts of the robot 16, such as to rotate the robot 16 about the vertical trunk 22 or to advance the mounting flange 36. The actuation assembly 12 may include a processor therein for storing operational commands and for transmitting digital signals to the electromechanical assembly 19. The actuation assembly 12 can also transmit electrical signals to the mounting flange 36 in the form of electrical signals for positioning and operating the DLU 18.

The actuation assembly 12 further transmits electrical signals to the electro-mechanical assembly 19 housed within the head portion 40 of the DLU 18 for actuating the electro-mechanical assembly 19 which in turn actuates the surgical tool 20. The electro-mechanical assembly 19 includes mechanisms for moving and operating the surgical tool 20, such as servo motors for harmonically oscillating a scalpel of a cutting DLU device, or rods for pivotally moving a suturing needle positioned on an axis of a longitudinal casing of a suturing DLU device. The DLU 18 may further include integrated circuitry, including a receiver 21 and a processor 23 for receiving digital signals from the actuation assembly. The receiver 21 and processor 23 are included within control means 25 electrically connected to the electro-mechanical assembly 19 as shown by FIG. 1A.

One type of electro-mechanical assembly can be used to advance, rotate and retract a coring portion 46 of a coring DLU device 48 as shown by FIG. 1. Coring DLU device 48 is suited for performing a coring procedure, such as coring body tissue for removing a specimen for biopsy, as shown by FIG. 2. The coring portion 46 includes a tubular member 50 having a cutting edge 52. The linear advancement of the tubular member 50 is automatically controlled by the electro-mechanical assembly 19.

When the coring DLU device 48 is actuated by transmitting electrical signals to the electro-mechanical assembly 19, the tubular member 50 can be distally and proximally moved by rods traversing the longitudinal axis of the coring portion 46 and operatively associated with the electro-mechanical assembly 19.

Figure 3:
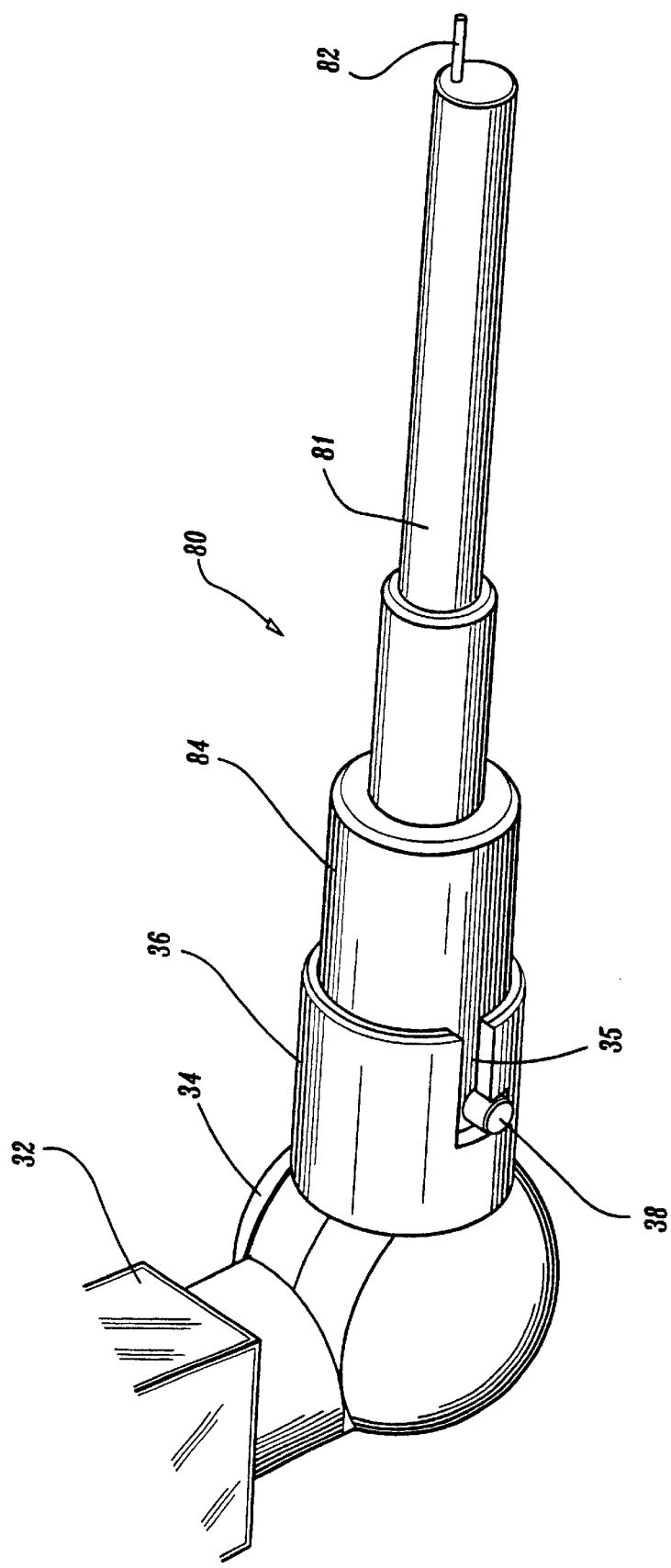
FIG. 3 is a perspective view of a lasing DLU device.

A lasing DLU device 80 is illustrated in FIG. 3 for performing surgical procedures requiring laser energy, such as a TMR procedure. Laser DLU device 80 includes a laser energy transmission mechanism 82 partially disposed within a body portion 81 and mounted for controlled longitudinal movement relative to a head portion 84 of the DLU 80. The actuation assembly 12 can be provided with a laser energy generator which is optically connected to the laser energy transmission mechanism 82 for initiating laser energy. The laser energy generator may also be incorporated within the electro-mechanical assembly 19. The laser energy transmission mechanism 82 typically includes at least one optical fiber for transmitting laser energy. The at least one optical fiber in the laser energy transmission mechanism 82 traverses the body portion 81 and is optically associated with the laser energy generator.

A controlled advancement mechanism is provided within the DLU head portion 84 and in engagement with the laser energy transmission mechanism 82 for advancing the laser energy transmission mechanism 82 at a controlled rate coordinated with the laser energy generator output to ablate body tissue. Controlled advancement mechanisms which can be incorporated within the head portion 84 include constant and/or variable rate springs, motors, and other mechanisms which can be coordinated with the laser energy generator to advance one or both of the laser energy transmission mechanism 82 during ablation.

Figure 4:
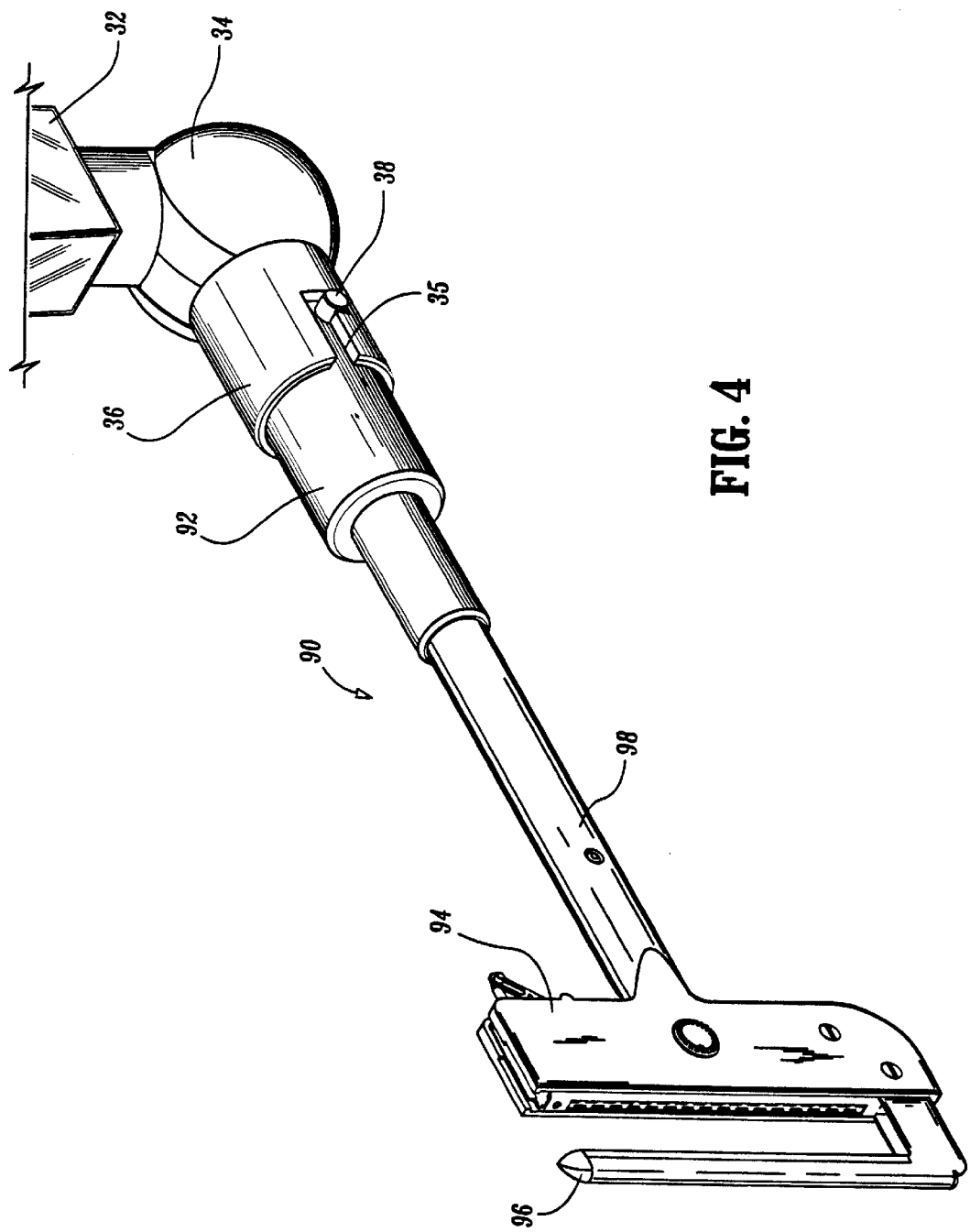
FIG. 4 is a perspective view of a surgical fastener applying DLU device.

A surgical fastener applying DLU device 90 is illustrated in FIG. 4 for applying an array of surgical fasteners to body tissue. Surgical fastener applying DLU device 90 includes an actuator incorporated within a head portion 92 to perform fast closure and incremental advancement of a cartridge assembly 94 with respect to an anvil assembly 96 at a distal end of body portion 98.

Reference can be made to U.S. Pat. No. 4,508,253 issued to Green on Apr. 2, 1985 or European Patent Application No. 92 116880.3 published on Apr. 21, 1993, the contents of both documents are incorporated herein by reference, for a more detailed explanation of the operation of the body portion components during a surgical fastening procedure. It is provided that the hand portion of the fastener applying apparatus disclosed in the '006 patent is incorporated within the structure and construction of the electro-mechanical assembly 19 of the surgical fastener applying DLU device 90 for operating the body portion components in the same manner as the hand portion operates the body portion components in the above-noted '006 patent.

FIG. 5 is a perspective view of a vessel clip applying DLU device 100 for applying surgical clips to body tissue. Vessel clip applying DLU device 100 includes a head portion 102, a body portion 104 extending distally from the head portion 102 and defining a longitudinal axis, and a plurality of surgical clips disposed within the body portion 104. A jaw assembly 106 is mounted adjacent a distal end portion 108 of the body portion 104. The jaw assembly 106 includes first and second jaw portions 110 movable between a spaced-apart and approximated position.

A clip pusher is provided within body portion 104 to individually distally advance a distal-most surgical clip to the jaw assembly 106 while the jaw portions 110 are in the spaced-apart position. An actuator 112 disposed within the body portion 104 is longitudinally movable in response to actuation of the electro-mechanical assembly 19 within the head portion 102. A jaw closure member 114 is positioned adjacent the first and second jaw portions 110 to move the jaw portions 110 to the approximated position. The actuator 112 and the jaw closure member 114 define an interlock therebetween to produce simultaneous movement of the actuator 112 and the jaw closure member 114 when the actuator 112 is positioned adjacent the distal end portion of the body portion 104.

Reference can be made to U.S. Pat. No. 5,300,081 issued to Young et al. on Apr. 5, 1994, the contents of which are incorporated herein by reference, for a more detailed explanation of the operation of the body portion components during a vessel clip applying procedure. It is provided that the hand portion of the vessel clip applying apparatus disclosed in the '081 patent is incorporated within the structure and construction of the electro-mechanical assembly 19 of the vessel clip applying DLU device 100 for operating the body portion components in the same manner as the hand portion operates the body portion components in the above-noted '081 patent.

With reference to FIG. 6A, a first embodiment of a cutting DLU device 120 is illustrated for cutting and storing sections of body tissue. Cutting DLU device 120 includes an actuator incorporated within a head portion 122, a body portion 124 having an outer tube 126 extending from the head portion 122, and a cutting tube 128 positioned within the outer tube 126 and movable in response to actuation of the electro-mechanical assembly 19 between a retracted position and a distal position to cut body tissue. The cutting tube 128 has a chamber 130 formed therein for storing the cut tissue sections.

A release lever is included within the electro-mechanical assembly 19 and is movable from a blocking position to allow the cutting tube 128 to be removed from the outer tube 126. An anvil 132 is positioned at a distal end of the outer tube 126 for forcing each cut tissue section proximally into the chamber 130 of the cutting tube 128 as the cutting tube 128 is advanced to cut the body tissue. The electro-mechanical assembly may include an oscillation assembly operatively associated with the cutting tube 128 to harmonically oscillate the cutting tube 128.

A second embodiment of a cutting DLU device 140 is shown by FIG. 6B. This embodiment includes a scalpel 142 which can be encased within a cylinder 144 capable of being moved proximally and distally. A harmonic oscillator may be incorporated within the head portion 146 to harmonically oscillate the scalpel 142. In addition, it is contemplated to provide mechanisms within the head portion 146 for rotating and longitudinally moving the scalpel 142.

With reference to FIG. 7, there is shown a hole-punching DLU device 150 for facilitating the formation of an elliptical hole in the aorta during a coronary artery bypass grafting (CABG) procedure. Hole-punching DLU device 150 includes a head portion 152 having an actuator therein for actuating an actuating rod 154 disposed in body portion 156 and mounted for longitudinal movement between an unactuated position and an actuated position, and a punch blade 158 disposed at the distal end of the actuating rod 154.

The distal end of body portion 156 includes an elliptical opening 157 to receive punch blade 158 when the actuating rod 154 is moved to the unactuated position. The elliptical opening 157 includes a sharp circumference for cutting tissue disposed between the distal end of body portion 156 and the punch blade 158 when the actuating rod 154 is moved proximally for forming an elliptical hole in a coronary artery for the performance of the CABG procedure.

Figure 8:
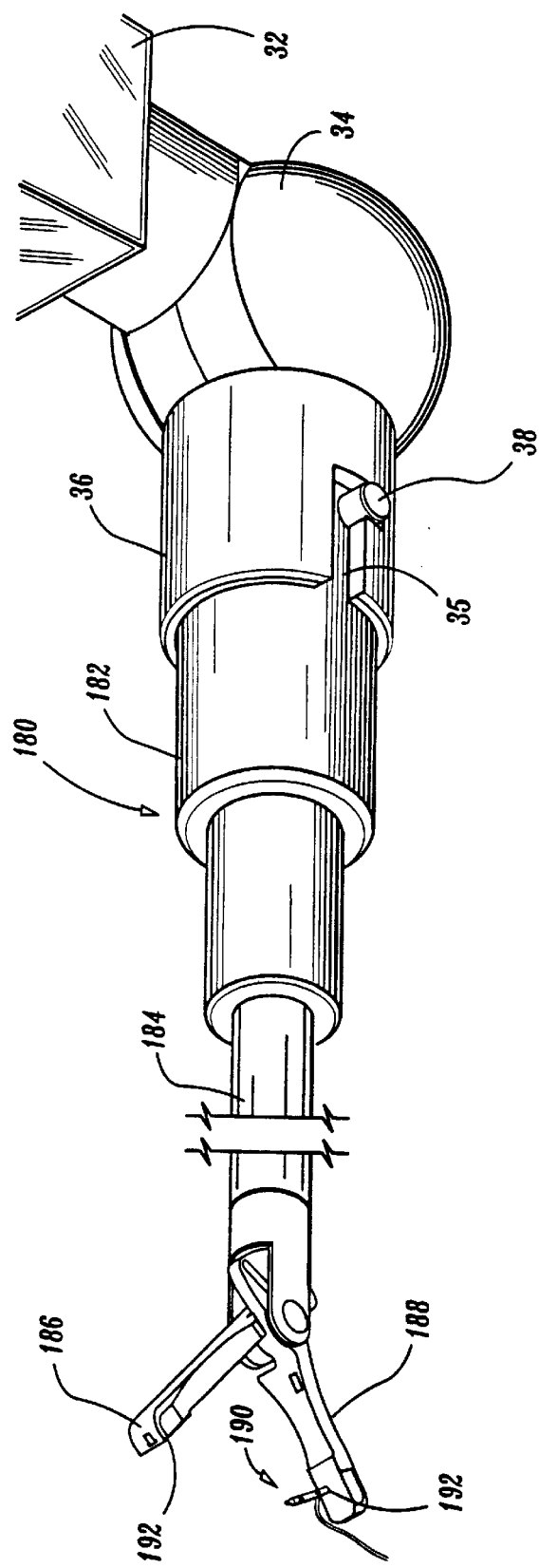
FIG. 8 is a perspective view of a vascular suturing DLU device.

Finally, with reference to FIG. 8, a vascular suturing DLU device 180 is illustrated for suturing vascular tissue sections together. Vascular suturing DLU device 180 includes a head portion 182 and a body portion 184 extended distally therefrom. A pair of needle receiving jaws 186, 188 are pivotally mounted at a distal end of the body portion 184 and are configured to repeatedly pass a surgical needle and associated length of suture material therebetween. The apparatus further includes needle holding structure 190 mounted within the jaws 186 for reciprocal movement into and out of needle holding recesses 192 formed in the jaws 186, 188. During an anastomosis procedure, the vascular suturing DLU device 180 will advantageously respond to movement commands transmitted from the actuation assembly to apply fasteners to tissue.

Reference can be made to U.S. Pat. No. 5,478,344 issued to Stone et al. on Dec. 26, 1995, the contents of which are incorporated herein by reference, for a more detailed explanation of the operation of the body portion components during a vascular suturing procedure. It is provided that the hand portion of the vascular suturing apparatus disclosed in the '344 patent is incorporated within the structure and construction of the electro-mechanical assembly 19 of the vascular suturing DLU device 180 for operating the body portion components in the same manner as the hand portion operates the body portion components in the above-noted '344 patent.

It is contemplated to have feedback forces initiated by pressure and other parameters indicative of the surgical task being performed by the at least one surgical tool of the DLU transmitted back through a microprocessor to a digital-to-analog circuit board. This force feedback control system allows the robotic system to be programmed before the surgical task is performed with guidance, pressure, and other parameters which can be continuously monitored to control the operation and movement of the DLU and of the at least one surgical tool.

While the invention has been illustrated and described as embodied in an apparatus and method for performing surgical tasks, it is not intended to be limited to the details shown, since it will be understood that various omissions, modifications, substitutions and changes in the forms and details of the device illustrated and its operation can be made by those skilled in the art without departing in any way from the spirit or scope of the appended claims.

What is claimed is:

1. A disposable loading unit configured for mounting to a robotic arm for performing at least one surgical task, the disposable loading unit comprising:

a) an attachment platform having at least one connector for releasably engaging at least one connector on a distal end of the robotic arm for attaching the disposable loading unit to the robotic arm and for establishing an electrical connection for receiving or transmitting at least one electrical signal;

b) a head portion connected to the attachment platform and adapted for electro-mechanical coupling to the robotic arm, the head portion being mounted for articulating movement with respect to a longitudinal axis of the robotic arm; and c) at least one surgical tool member extending from the head portion and operatively associated with the electro-mechanical assembly for performing the at least one surgical task.

2. A disposable loading unit as recited in claim 1, wherein the at least one surgical tool member is selected from a group consisting of a cutting assembly, an aortic hole punch assembly, a lasing assembly, a coring assembly, or a vascular suturing assembly.

3. A disposable loading unit as recited in claim 1, wherein the at least one surgical tool member is configured for endoscopic surgical tasks.

4. A disposable loading unit as recited in claim 1, wherein the at least one surgical tool member is configured for laparoscopic surgical tasks.

* * * * *